United States Patent [19]

Leigh

[11] Patent Number: 5,141,674

[45] Date of Patent: Aug. 25, 1992

[54] METHODS OF PREPARING PRO-LIPOSOME DISPERSIONS AND AEROSOLS

[75] Inventor: Steven Leigh, London, United Kingdom

[73] Assignee: Phares Pharmaceutical Research N.V., Curacao, Netherlands Antilles

[21] Appl. No.: 719,661

[22] Filed: Jun. 24, 1991

Related U.S. Application Data

[63] Continuation of Ser. No. 282,340, Nov. 30, 1988, abandoned, which is a continuation of Ser. No. 709,796, Aug. 3, 1985, abandoned, and Ser. No. 171,148, Mar. 21, 1988, Pat. No. 5,004,611, which is a continuation-in-part of PCT/GB87/00391, Jun. 5, 1987.

[30] Foreign Application Priority Data

Jun. 6, 1986 [GB] United Kingdom ............... 8613811

[51] Int. Cl.$^5$ .................... A61K 9/12; A61K 9/127; B01J 13/02
[52] U.S. Cl. .................................. 252/305; 424/450; 424/45; 424/40; 424/47; 264/4.1; 427/213.3
[58] Field of Search ............... 264/4.1, 4.3, 4.6; 424/450, 45, 47, 40; 427/213.3; 252/305

[56] References Cited

U.S. PATENT DOCUMENTS

| | | | |
|---|---|---|---|
| 4,229,360 | 10/1980 | Schneider et al. | 424/450 |
| 4,370,349 | 1/1983 | Evans et al. | 514/785 |
| 4,508,703 | 4/1985 | Redziniak et al. | 264/46 X |
| 4,830,858 | 5/1989 | Payne et al. | 424/450 |
| 5,004,611 | 4/1991 | Leigh | 424/450 |
| 5,049,388 | 9/1991 | Knight et al. | 424/450 |
| 5,053,217 | 10/1991 | Leigh | 424/45 |

FOREIGN PATENT DOCUMENTS

| | | | |
|---|---|---|---|
| 158441 | 10/1985 | European Pat. Off. | |
| 8601714 | 3/1986 | PCT Int'l Appl. | 424/450 |
| 8701586 | 3/1987 | PCT Int'l Appl. | |
| 2135268 | 8/1984 | United Kingdom | 424/450 |
| 2135647 | 9/1984 | United Kingdom | 424/450 |

*Primary Examiner*—Robert L. Stoll
*Assistant Examiner*—John M. Covert
*Attorney, Agent, or Firm*—Klauber & Jackson

[57] ABSTRACT

Compositions that are sprayable or that are in the form of discrete particles and that contain a lipid and a biologically active compound in the form of a micronized powder combine a high initial entrapment of the active compound in the membrane lipid with sustained release at the site of application as indicated by in-vitro and in-vivo tests. In a first form pro-liposomes are prepared by spraying under pressure through a nozzle a single composition comprising at least one volatile liquid propellant, at least one membrane lipid that is at least partly dissolved or dispersed in the propellant and at least one biologically active compound that is present in dispersion in the propellant and/or the lipid, the composition being free from other solvent for the lipid. In a second form the membrane lipid and the biologically active compound are minor components of micronized solid particles whose major component is a physiologically acceptable solid carrier.

31 Claims, 6 Drawing Sheets

METHODS OF PREPARING PRO-LIPOSOME DISPERSIONS AND AEROSOLS

This application is a continuation of application Ser. No. 07/282,340, filed Nov. 30, 1988, now abandoned, which is a continuation application of U.S. Ser. No. 06/709,796 filed Aug. 3, 1985 which is now abandoned and co-pending U.S. Ser. No. 07/171,148 filed Mar. 21, 1988, now U.S. Pat. No. 5,004,611, and a continuation-in-part application of my international application No. PCT/GB87/00391 filed Jun. 5, 1987, as amended on May 23, 1988 for which priority is claimed under Title 35 USC 119 as GB 8613811 filed Jun. 6, 1986.

This invention relates primarily to a composition based on a membrane lipid and at least one biologically active compound in the form of a micronised powder and to a method of making a progenator of liposomes or pro-liposome in the form of an aerosol or discrete particles.

Membrane lipids are lipids which form bilayers with water; they are chiefly phospholipids such as lecithin and related materials such as glycolipids. Phospholipid vesicles are also known as liposomes. In addition to naturally occurring membrane lipids, synthetic bilayer-forming materials may also form similar vesicles known as niosomes. According to the general nomenclature, all types of lipid bilayers surrounding an aqueous space are generally known as liposomes which term shall include niosomes. The promise held out by liposomes as a means of delivering and targeting drugs has, not surprisingly, prompted intensive research into this subject.

Our European Patent Application No. 85301602 describes pro-liposome compositions that spontaneously form vesicles or liposomes in the presence of excess water and that may be presented *inter-alia* in sprayable form. Thus there are provided aerosol compositions comprising in a volatile liquid propellant:

(a) at least one membrane lipid;
(b) at least one water-miscible liquid which is a solvent for the lipid; and
(c) up to 40%, by weight on the combined weights of a), b) and c), of water;

the proportion by weight of a) to b) being from 40:1 to 1:20.

This invention is based on the realisation that sprayable compositions or compositions in the form of discrete particles containing a bilayer lipid and a biologically active compound in the form of a micronised powder combine high initial entrapment of the active compound in the lipid with sustained release at the site of application.

AEROSOL COMPOSITIONS

It has been found that pro-liposomes may be made in the form of aerosols of at least one membrane lipid and at least one biologically active compound, the aerosol being free from other solvents. Further advantages of this type of composition include freedom from unnecessary solvents or water, more control over particle size and improved stability.

A preferred method of forming the pro-liposome aerosols is by spraying under pressure a single composition which comprises at least one volatile liquid propellant, at least one membrane lipid that is at least partly dissolved or dispersed in the propellant and at least one biologically active compound that is present as a micronised powder dispersed in the propellant and/or the lipid, the composition being free from other solvent for the drug.

The invention further provides a sprayable pro-liposome composition at comprising at least one volatile liquid propellant, at least one membrane lipid that is at least partly dissolved or dispersed in the propellant and at least one biologically active compound that is present as a micronised powder dispersed in the propellant and/or the lipid, the composition being free from other solvent for the lipid.

It is well known that biologically active compounds can be incorporated into liposomes partly to protect and partly to enhance their activity as mentioned in our European Patent Specification No. A-0158441. One of the features of this invention is the relative ease with which high levels of drug or other biologically active compound can be associated with liposomes.

It has been demonstrated by in-vitro tests that pro-liposome compositions according to the present invention not only enable high initial entrapment of drug, but surprisingly, also provide for sustained release of the drug at the site of application. It has been found quite unexpectedly that compositions according to the present invention are superior to previously known liposome and pro-liposome aerosol compositions in prolonging the action of drugs at the site of action. Accordingly the compositions of (or made according to) the invention are particularly suitable for bronchial, pulmonary, and nasal inhalation treatments. They are also suitable for oropharyngeal and topical applications where prolonged effects are desirable to minimise frequency of dosage. Combinations of lipid and drug incorporated into the composition will preferably have the proper electrical charges. Most naturally occurring phospholipids are negatively charged. Some, especially those that are electrically neutral, may require addition of minor amounts of compatible organic materials that can confer the required charge on them. A negative charge can be imparted to the lipid material by adding, for example, phosphatidic acid or dicetyl phosphate, and a positive charge can be imparted by adding an amine such as stearylamine.

The proportion of lipid in the composition is desirably as small as possible (in order to minimise the risk of clogging the orifices of the spray canister) but concomitant with obtaining the optimum level of drug association. The weight ratio of drug to lipid will depend on the activity of the drug and may typically be from 1:0.5 to 1:25, more usually 1:1 to 1:24 and preferably from 1:6 to 1:12. For highly potent drugs, the appropriate drug/lipid ratio may be above 1:25.

The volatile liquid propellant used in the sprayable compositions of the invention may be butane or dimethylether, in circumstances where its use is permitted, but is preferably a perhalocarbon, particularly Arcton 11 ($CClF_3$), Arcton 12 ($CCl_2F_2$) or Arcton 114 ($C_2Cl_2F_4$). The propellant generally constitutes from 75% to 99%, usually from 87% to 97% by weight of the overall composition.

Suitable membrane lipids are phospholipids, for example, phosphatidyl choline, such as soy lecithin and egg yolk lecithin and synthetic lecithins, e.g. di-palmitoyl phosphatidyl choline. Other materials such as glycolipids may be used. Other bilayer-forming materials that can be used include long-chain dialkyl dimethyl ammonium compounds, for example di-stearyl dimethyl ammonium compounds such as di-stearyl dimethyl ammonium chloride, di-tallow dimethyl ammonium compounds such as di-tallow dimethyl ammonium chloride and mono- and dialkyl polyoxyethylene derivatives, although possible irritancy may limit their use to non-inhalation applications. In this text, the generic term lipid is used to describe all such bilayer-forming compounds.

Most biologically active compounds can be incorporated into the sprayable composition. In most instances the biologically active compounds should be insoluble or only sparingly soluble either in the lipid or in the propellant. Accordingly they are incorporated into the composition in the form of micronised powders of mean particle size in the range of from 0.5 micron to 8 microns, preferably from 1 micron to 5 microns.

Specific biologically active compounds dispersed in the lipid are effective as bronchodilators, steroids, antibiotics, antihistamines, vasoconstrictors and anti-inflammatory compounds. Examples of such compounds are salbutamol, terbutaline, orciprenaline, isoprenaline, reproterol, pirbuterol, butenoside, beclamethasone dipropionate, sodium chromoglycate, fenoterol, ipratropium, betamethasone valerate, rimiterol or ketotifen.

On being sprayed, e.g. from an aerosol container, the propellant preferentially volatilises, leaving an aerosol of the remaining components as a pro-liposome composition in the form of droplets of a size determined by the spray nozzle and internal pressure and preferably below 8 microns. On contacting water, these droplets form a dispersion of liposomes which constitute very effective drug carriers.

POWDER COMPOSITIONS

A second method of making the pro-liposome aerosol is from micronised solid particles whose major component is a physiologically acceptable solid carrier and whose minor components are the biologically active compound in particulate dispersion in the lipid. Glucose or lactose are suitable solid carriers and being water-soluble, they dissolve on contact with a moist surface such as a biological membrane. However, hydrophillic materials such as polysaccharides (dextrans and starches), polymers (polyethylene), proteins (albumen, casein) and soluble collagen may be suitable for non-inhalation applications as long as they are free-flowing micronised powders, and compatible with the lipid.

The weight ratio of membrane lipid to carrier is suitably from 1:1 to 1:25, preferably from 1:5 to 1:20. The ratio of drug to lipid is as before. The powder aerosol may be formed by vibrating or propelling the particles from a capsule (as in a spinhaler type device) into a moving airstream.

It has been found that high levels of entrapment and improved in-vitro release profiles are obtained when the biologically active compound is in micronised dispersion in the lipid. Dispersion/suspension of the drug is assisted if the lipid is first dissolved in a volatile solvent which is not a solvent for the drug. Perhalocarbons which are conventionally used as propellants, particularly Arcton 11, are suitable because they are inert and are usually poor solvents for most biologically active compounds. However, depending on the properties of the powder and the drug, other lipid solvents eg. chloroform or dimethyl ether may be used. The solid carrier must not be soluble in the solvent. Alcohol or methanol would be less suitable if the drug is substantially soluble.

The solvent is evaporated off completely either before or after addition of the solid carrier. The resulting powder composition comprises a uniform mixture of solid particles whose major component is a physiologically acceptable solid carrier and whose minor components are the biologically active compound in particulate dispersion in the lipid.

In contrast, the powder compositions described by Payne et al (Journal of Pharmaceutical Sciences, Vol. 75, No. 4, Apr. 1986) require the drug to be in solution in the lipid. A 2:1-methanol/chloroform solution of the drug is loaded onto the powder under carefully controlled conditions. It is reasonable to assume that the solid carrier would be evenly loaded with a coating of lipid and drug in solution. They confined their studies to *coarse* powders in the range 75 to 600 microns and concluded that their pro-liposome system was ideally suited for so-called lipophillic actives.

We have found that this method gives rise to compositions which may have high initial association (60% –70%). However, our in-vitro studies have indicated that they do not retain the biologically active compound, whose release profile is quite different, and characterised by uncontrolled release of the active compound into the aqueous phase.

The invention will be illustrated by the following 20 examples.

EXAMPLE I

Sprayable compositions and entrapment of Fenoterol therein

The following sprayable compositions were made up using soya bean lecithin (SBL), a 23:54:23 parts by weight mixture of Arcton 114, Arcton 12 and Arcton 11 as propellant and micronised fenoterol as its free base or hydrobromide as biologically active compound.

The lipid was initially dissolved in a small quantity of Arcton 11. Micronised fenoterol was dispersed in this solution. The rest of the propellant mixture was added to the suspension. The composition was filled into 20 ml aerosol containers fitted with metered heads delivering a nominal 65 $\mu l$.

The samples were used to form pre-liposome aerosols that were allowed to form liposomes by contact with excess water. The % of fenoterol associated with each liposome dispersion was evaluated by the procedure described below.

The aerosol pro-liposome compositions of samples 1 to 5 were sprayed from canisters which contained no dip tube into a phosphate buffer solution (pH7). One gram of propellant/drug/lipid pro-liposome was sprayed into 50 ml of buffer contained in a 250 ml flask adapted to receive the inverted aerosol container above. Liposome suspensions were formed spontaneously as the aerosol mist encountered the buffer solution. The flask was gently swirled to contact the suspended aerosol with the buffer. This process was repeated until the aerosol canister had been drained of one gram of its contents. Fenoterol was assayed as follows. The fenoterol/liposome suspension was centrifuged at 180,000 g for 90 minutes. The supernatant was assayed for free drug by measuring absorbance at 276 nm. The liposomal pellet containing trapped fenoterol was resuspended in 1% nitric acid to release bound drug and assayed as before. The percentage of drug associated with the liposomes was calculated accordingly.

The entrapment results for each of the five samples are indicated in Table I below.

TABLE I

| Sample No | Propellant Wt (g) | Drug Wt (g) | SBL Wt (Mg) | % SBL Associated Initial Entrapment HBr | % SBL Associated Initial Entrapment Base |
|---|---|---|---|---|---|
| 1 | 9 | 50 | 50 | 15 | 15 |
| 2 | 9 | 50 | 150 | 42 | 35 |
| 3 | 9 | 50 | 300 | 60 | 45 |
| 4 | 9 | 50 | 600 | 75 | 57 |
| 5 | 9 | 50 | 1200 | 85 | 72 |

EXAMPLE II

Investigation of the effects of lipid-drug ratio on sustained release properties in-vitro Factors relevant to the sustained release of fenoterol in-vitro were investigated as follows. Fixed weights of aerosol were sprayed into a large conical flask containing 50 ml of phosphate buffer. The flask was vented at frequent intervals to prevent the build up pressure from vapourised propellant. The final concentration of fenoterol hydrobromide in the test suspension was normally about 0.5 mg/ml but measurements can be made using drug concentrations as low as 0.05 mg/ml. The test suspension was incubated at 37° C. Samples were removed at intervals and centrifuged for 30 min at 175,000 xg to pellet the lipid fraction. The concentration of fenoterol in the supernatant fraction was then measured by HPLC. The percentage of drug retained in the lipid fraction was calculated by comparison with the total fenoterol content of a similar non-centrifuged sample in which the lipid had been solvated in excess methanol. This data was then used to plot delayed release profiles of the different samples.

Figure 1:
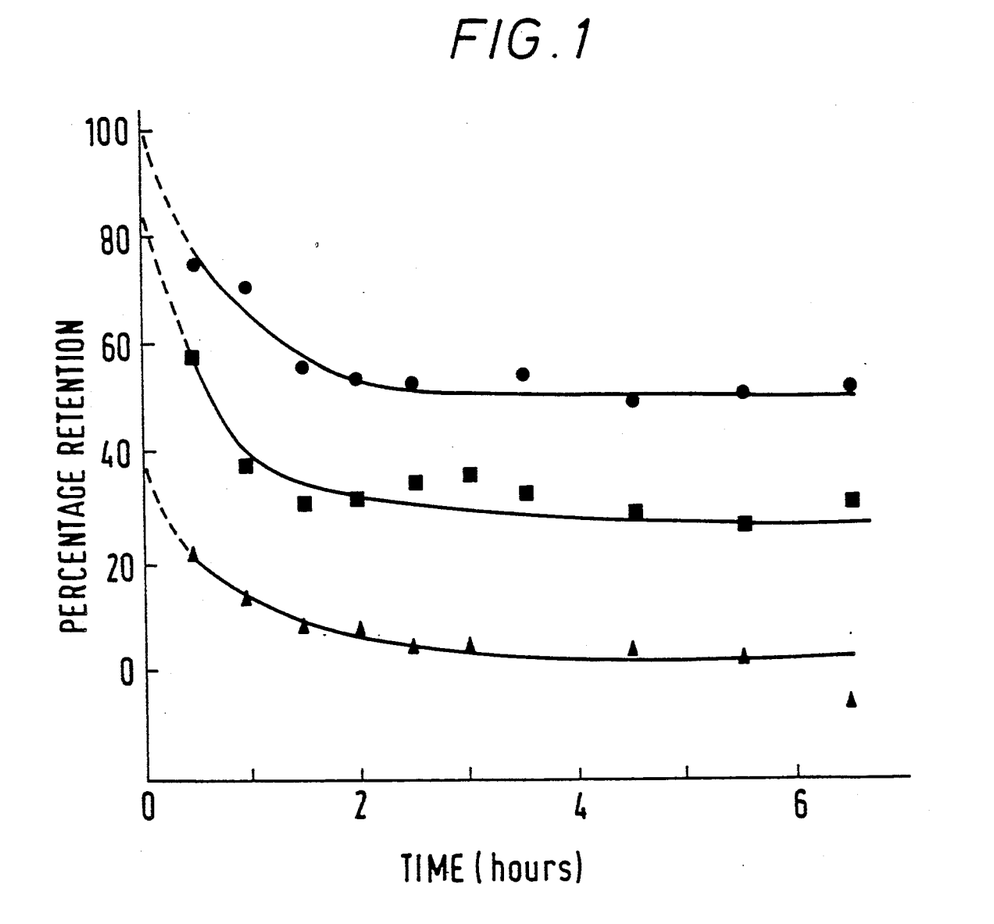
FIG. 1 illustrates the percentages retention of drug (fenoterol hydrobromide plotted as a function of time (hours) for type I aerosols prepared from standard lipid I with lipid: drug ratios of 12:1 (circles), 6:1 (squares), and 3:1 (triangles).
Figure 2:
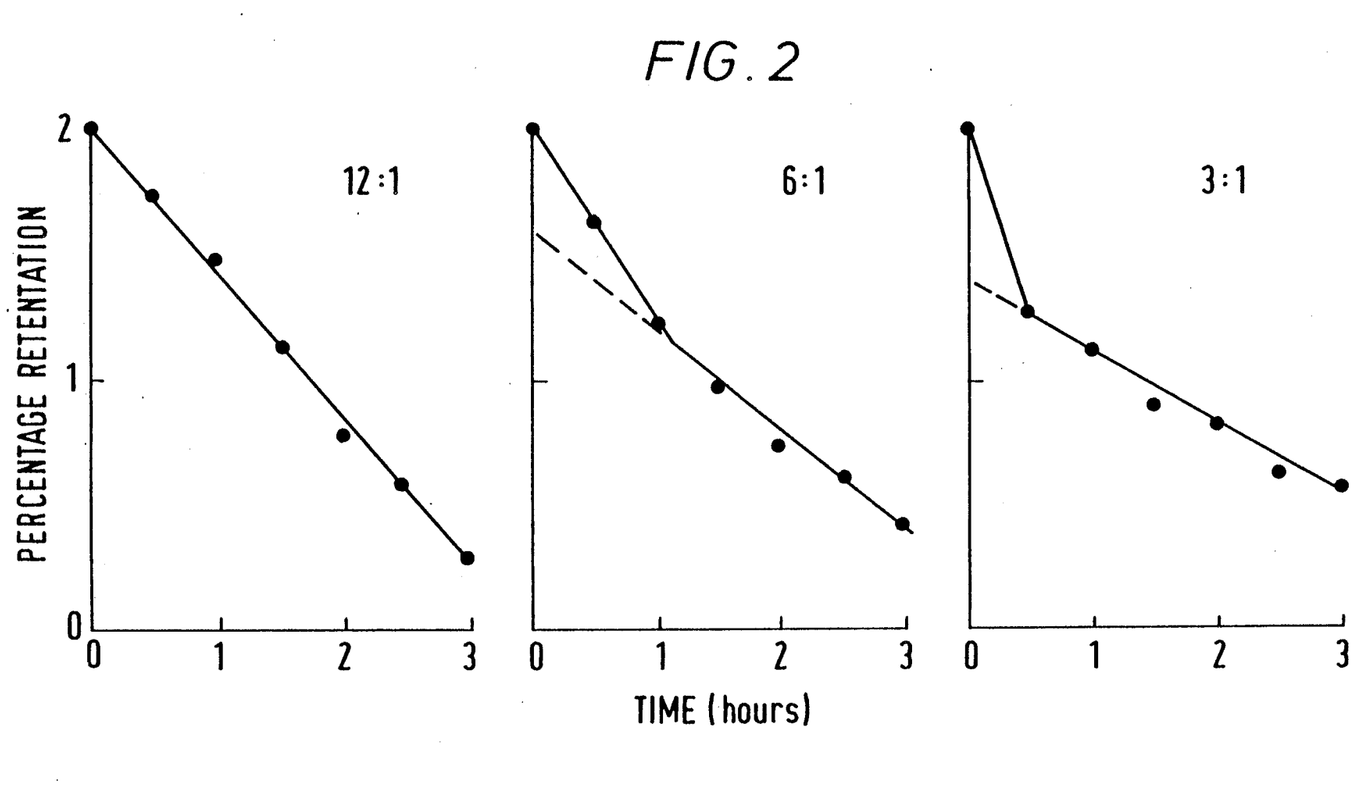
FIG. 2 is a three character semi-logarithmic plot of percentage retention against time for the different samples of the lipid: drug ratio shown.

The effects of altering the ratio of standard lipid I (95% pure soya bean lecithin) to fenoterol hydrobromide on the release profiles of our samples are illustrated in FIG. 1 in which percentage retention of fenoterol is plotted as a function of time in hours for so-called Type I aerosols prepared from standard lipid I with lipid:drug ratios of 12:1 (circles), 6:1 (squares) and 3:1 (triangles). The descending form of the curves denotes an initial high association between the fenoterol and the lipid phase, a subsequent slow release of part of the fenoterol into the aqueous medium and an eventual steady state determined by the partition coefficient between aqueous and lipid phases. The main effect of increased lipid content, apart from changing the final equilibrium position, was to alter the proportion of drug released within the first 30 min after spraying. Unfortunately, the time involved in sample preparation and centrifugation precluded an analysis of the release characteristics over this period. However, the results suggested that there was an initial very rapid release from solvated droplets followed by a slower release over a period about three hours before equilibrium was reached. This was more clearly demonstrated in the three semi-logarithmic plots of percentage retention against time for the different samples presented in FIG. 2.

EXAMPLE III

Effect of Lipid Modifiers

The inclusion of materials that might be expected to affect the lipid phase was investigated in-vitro. The effects of including cholesterol (33 mol %) and the saturated triglyceride glycerol tripalmitate (33 wt. %) in 12:1 lipid/drug formulations was investigated by determining percentage retention of fenoterol as a function of time for Type I aerosols of 12:1 drug/lipid ratio made from standard lipid, mixtures of standard lipid with cholesterol 33 mol %, standard lipid and glycerol tripalmitate 33 wt % and standard lipid and SPAN 40 (10 wt %). The effects of adding the surfactant SPAN 40 (10 wt. %) which might be expected to hasten hydration are shown for comparison. In practice, all the modifiers appeared to bring about increased rates of drug release in-vitro. The precise reasons for this are not clear. The most probable explanation, however, is that their different solubilities in the aerosol propellant resulted in the precipitation of the lipid as a phase-separated rather than a homogeneous mixture and that this leads to changes in the structural characteristics in the lipid droplets. However, in certain situations the use of standard modifiers need not be excluded.

EXAMPLE IV

Use of Different Lipids

The effects on sustained release of fenoterol of using two grades of soya bean lecithin (standard lipid I and II); purified egg yolk lecithin (EYL), purified hydrogenated lecithin, EYL+phosphatidyl choline, and EYL+phosphatidyl serine were investigated using the techniques outlined above. Fenoterol was released from such preparations extremely quickly. This extreme leakiness could be associated with the fact that the hydrogenated lipids tend to be in the gel rather than the liquid crystalline state at 37° C. However, addition of cholesterol, which tends to disrupt gel-phase lipid, led to little or no-improvement in the sustained release capacities of the preparations suggesting that other factors may be influencing their properties.

A particularly striking feature of the measurements performed using hydrogenated lipids is the extremely low interaction between the lipid and the drug. Earlier experiments have suggested that the higher the purity of the lipid, the less strongly bound the drug. In order to test whether the lack of binding of the hydrogenated lipids was associated with their hydrogenation or their high purity, we performed a series of experiments using highly purified lecithin (Lipid Products, Grade 1) standard lipid I (95% pure soy-bean lecithin) and another grade of partially purified lecithin (Lipid II). It was clear from measurements obtained that the Lipid I and Lipid II preparations performed better in terms of delayed release than the highly purified lipid. This result probably reflected the presence in the samples of species providing extra drug binding sites. The most likely candidates for such a species were the acidic lipids phosphatidyl-ethanolamine and phosphatidylserine. We therefore prepared mixtures of purified lecithin together with 25 mol % of these lipids. Delayed release profiles of these samples showed that inclusion of the acidic lipids led, in both cases, to an increase in drug binding resulting in higher final equilibrium levels but the effects were more marked for phosphatidylserine than for phosphatidylethanolamine. The presence of these lipids, however, did not seem to delay the initial fast release characteristics of the purified lipid. This result was in agreement with studies using negative amphipaths such as dicetyl phosphate. The inclusion of such materials appeared to increase the partition of fenoterol into the lipid phase giving rise to high initial association but also tended to increase leakage rates.

EXAMPLE V

Structure of the Lipid Droplets Delivered by the Aerosols

Figure 3:
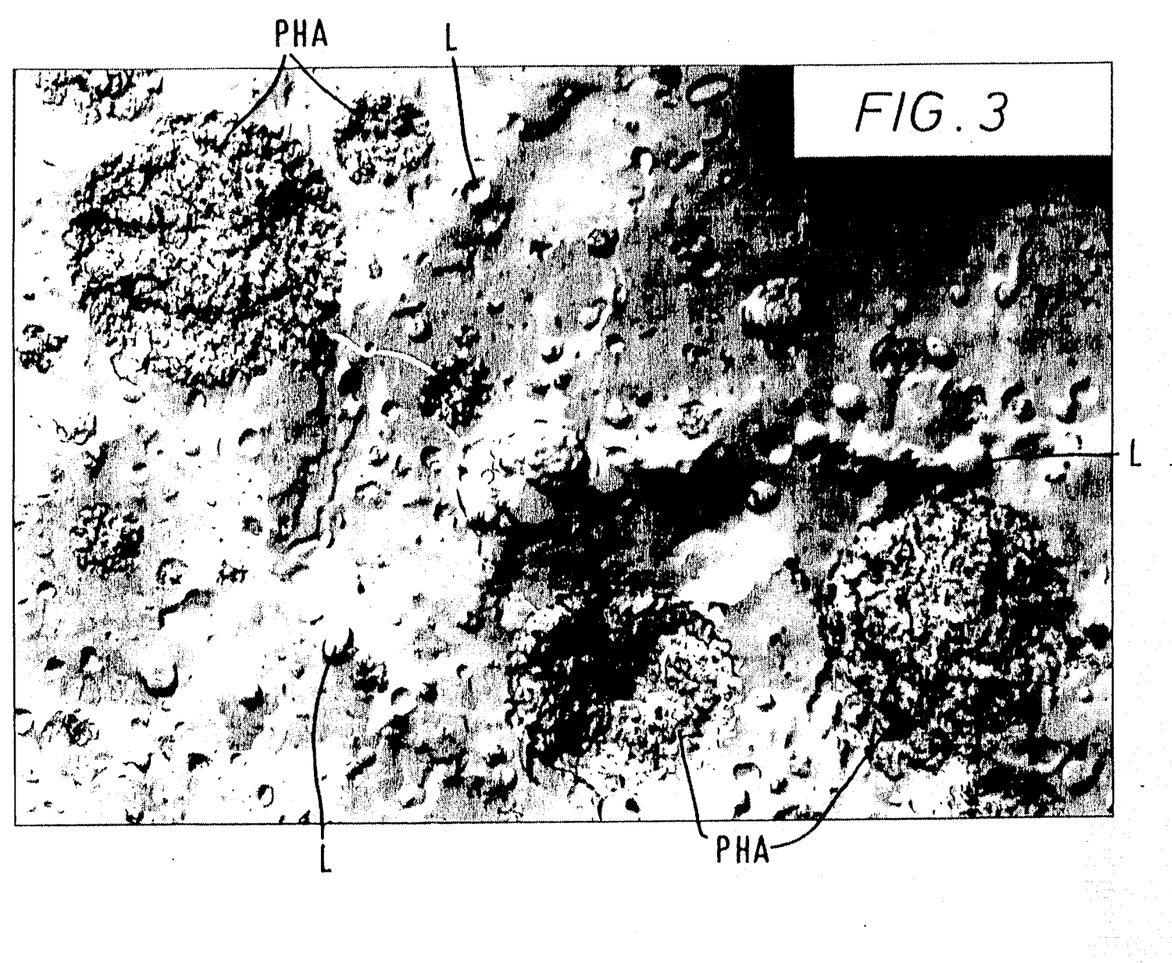
FIG. 3 depicts an electron microscopic image of a typical aggregate field of droplets of liposomal structures delivered by aerosol (scale 1 cm = 1.1M).

The compositions readily formed liposomes when sprayed onto an aqueous surface. Examination by freeze-fracture electron microscopy revealed a mixture of partially hydrated lipid aggregates and liposomes. The lipid aggregates appeared to be composed of lipid in the process of hydration and were likely to reorganise into liposomes on standing. FIG. 3 which is on a scale of 1 cm equals 1.1 $\mu M$ shows a typical field of liposomal structures formed on spraying a Type I aerosol containing fenoterol into water. The field contained liposomes (L) and partially hydrated liquid aggregates (PHA). The EMs shown in FIG. 3 clearly showed liposomes in the process of budding-off from such an aggregate. The possibility that some solid fenoterol particles were associated with the lipid aggregates in FIG. 3 could not be excluded. These might have acted as nuclei for the formation of lipid aggregates and hence functioned as reservoir of solid drug which would gradually have released the drug over a period of time. We believe that at the site of application (in-vivo) the majority of particles initially deposit as PHA followed by a gradual rather than an instantaneous process of conversion into liposomes.

EXAMPLE VI

Spray Characteristics

Figure 4A:
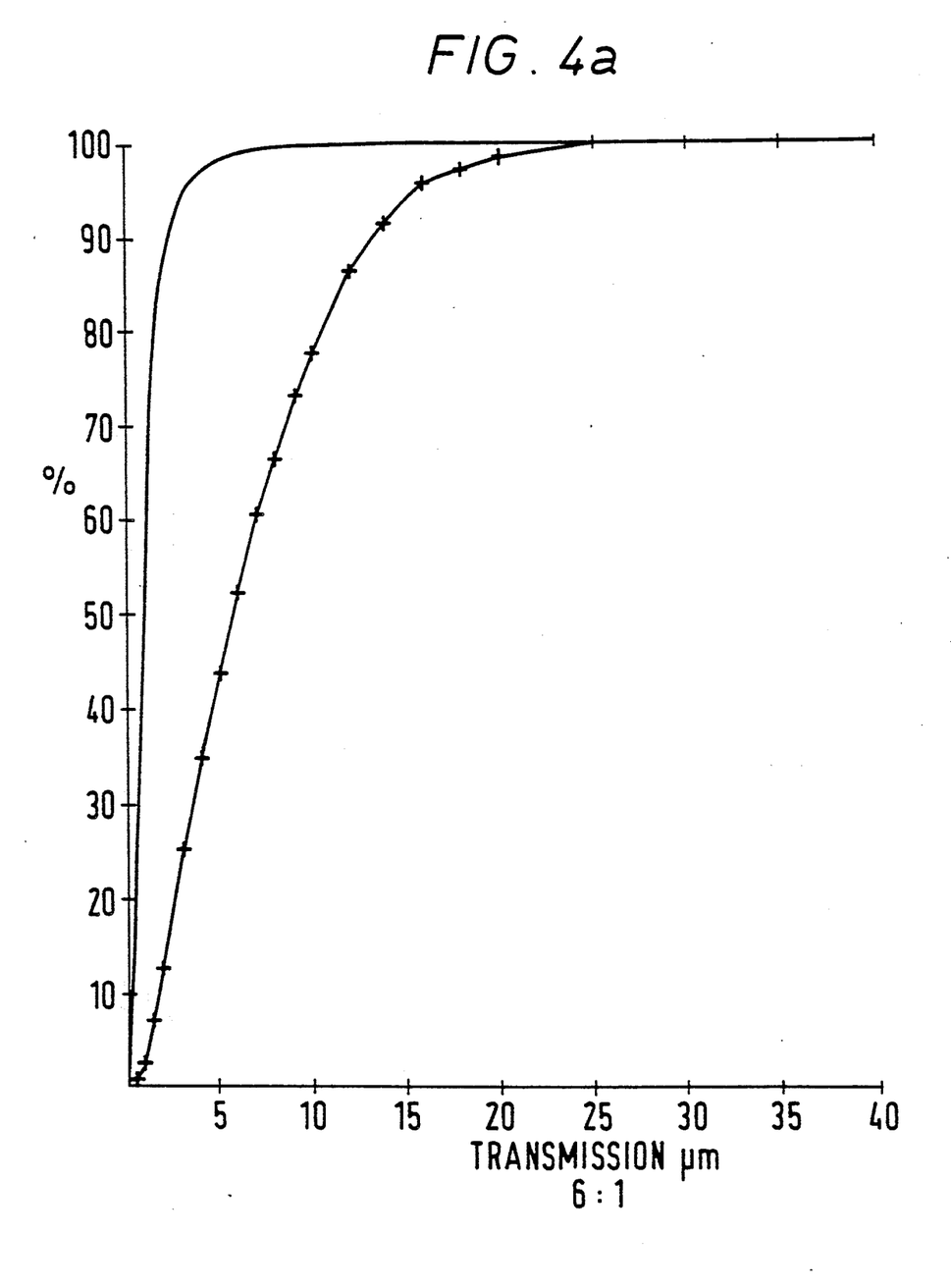
FIGS. 4a and 4b depict spray characteristics and droplet size of the effect of lipid/drug ratios.
Figure 4B:
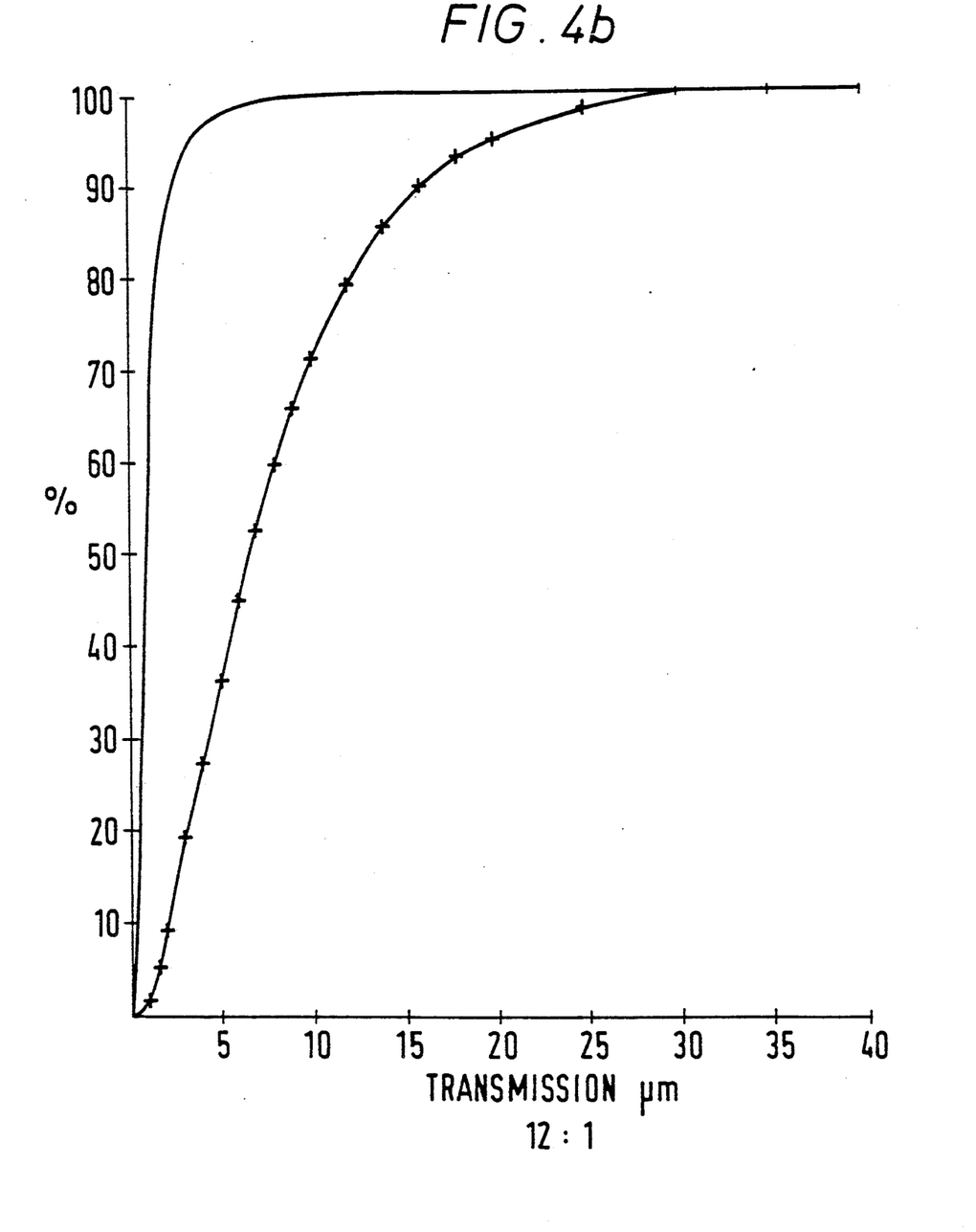

For inhalation applications, it is desirable that the majority of the droplets should be predominantly in the 2 to 7 micron range. Only particles in this range are capable of reaching the lower regions of the lung. Measurements of the droplet size from two compositions with lipid/drug ratios 6:1 and 12:1 were carried out in a Laser Beam Droplet & Particle Size Analyser (Malvern Instruments). FIGS. 4a and 4b show the effect of lipid/-drug ratios on droplet size. The mean proportion of droplets of particle diameter below 7.5 $\mu$ is seen to decrease from a cumulative value of about 65% to 55% as the lipid/drug ratio increases from 6:1 (FIG. 4a) to 12:1 (FIG. 4b).

In order to determine the proportion of the drug dose delivered within the respirable range, measurements were made using a cascade impactor (C. F. Casell and Co., London). This type of cascade impactor consists essentially of a system of four air-jets impinging in series on glass discs. The successive jets are progressively finer, so that the speed and, therefore, the efficiency of impaction of particles on to the discs increases from jet to jet, when air is drawn through at a steady rate. A size-grading thereby results which is used to assess the samples.

The drug collected on Plate 1 (particle range 7-20 $\mu m$ diameter) was assumed to be contained within droplets that would be too large to be inhaled. Droplets in this size range would normally be expected to impact on the throat and be ingested. Drug collected on Plate 4 (particle range up to 0.7 $\mu m$ diameter) was assumed to be contained in drops so small that they would probably be immediately exhaled. Only drug collected on Plates 2 and 3 (particle range 0.7-7.0 $\mu m$) was considered to lie within the respirable range.

A series of sprays (12:1 lipid/drug ratio) were prepared, which had vapour pressures ranging from 41 psi to 64 psi, the highest pressure at which samples could easily be prepared (by using different proportions of Arcton 11 and 12). These formulations were sprayed into the cascade impactor through which an air-flow of 17.5 liters per minute was being drawn. Each formulation was sprayed through a 0.75 mm nozzle and also through one with a finer orifice (0.5 mm). The amounts of drug impacting on Plates 3 and 4 were determined by HPLC. The results of these measurements are presented in Table II.

TABLE II

RESPIRABLE DOSE (ug) DELIVERED PER ACTUATION BY TYPE 1 (12:1) AEROSOLS FITTED WITH DIFFERENT NOZZLES MEASURED AT DIFFERENT PROPELLANT VAPOUR PRESSURES

| Sample | Vapour Pressure (psi) | | | | |
| --- | --- | --- | --- | --- | --- |
|  | 41 | 47 | 51 | 55 | 60 |
| Standard Nozzle (at least 0.75 mm) | 12.4 | 8.7 | 14.9 | 10.6 | 13.1 |
| Small Nozzle (0.5 mm) | 22.6 | 16.4 | 20.7 | 23.7 | 25.8 |

They indicate that changes in vapour pressure have little effect on the fraction of the original dose delivered in the respirable range using the same nozzle size. Increasing the vapour pressure of the samples did, however, decrease the 7-20 micron component. The biggest improvement in drug delivery was attained using the smaller nozzle. This was evident at all the vapour pressures employed.

On the basis of these measurements, applicants are of the opinion that by selecting an appropriate combination of vapour pressure and nozzle size the delivery of pro-liposome droplets within the respirable range can be maximised.

EXAMPLE VII

In-vitro Sustained Release Comparisons

The sustained release properties of the compositions according to the invention have so far been demonstrated under in-vitro conditions. The data obtained provide good evidence that the present invention provides for the sustained release of a biologically active compound. It has also been demonstrated that the compositions of the invention are at least as effective as pro-liposome aerosol compositions disclosed in our earlier publication EP-A-0158441 in delaying the release of a biologically active compound. A composition according to the present invention, designated Type I, 
was tested against two other formulations (Type II and Type III) disclosed in publication EP-A-0158441.

TYPE I:

A composition according to the present invention where the micronised drug is *dispersed* uniformly in a blend of Arcton 11, 12 and 114, having dissolved therein a lipid.

TYPE II:

In this example, the biologically active compound was dissolved in a pro-liposome composition containing a small quantity of alcohol as solvent for the biologically active compound. The propellant was the same as in Type I.

TYPE III:

In this example the drug was dissolved in a pro-liposome composition which contained both alcohol and water. The propellant was the same as in Types I and II.

Liposomal suspensions of all three formulations were formed in-situ by spraying into an aqueous reservoir as previously described.

In this experiment, the release of drug from the liposomal suspensions was determined in a diffusion cell. The preparation was placed on one side of a 4 cm diameter dialysis membrane in the cell. Buffer was pumped through a narrow space under this membrane at a fixed rate of 2 ml per minute. The solution emerging from the membrane cell was returned to the reservoir for recirculation. The rate of diffusion of the drug through the membrane was monitored by HPLC.

Figure 5:
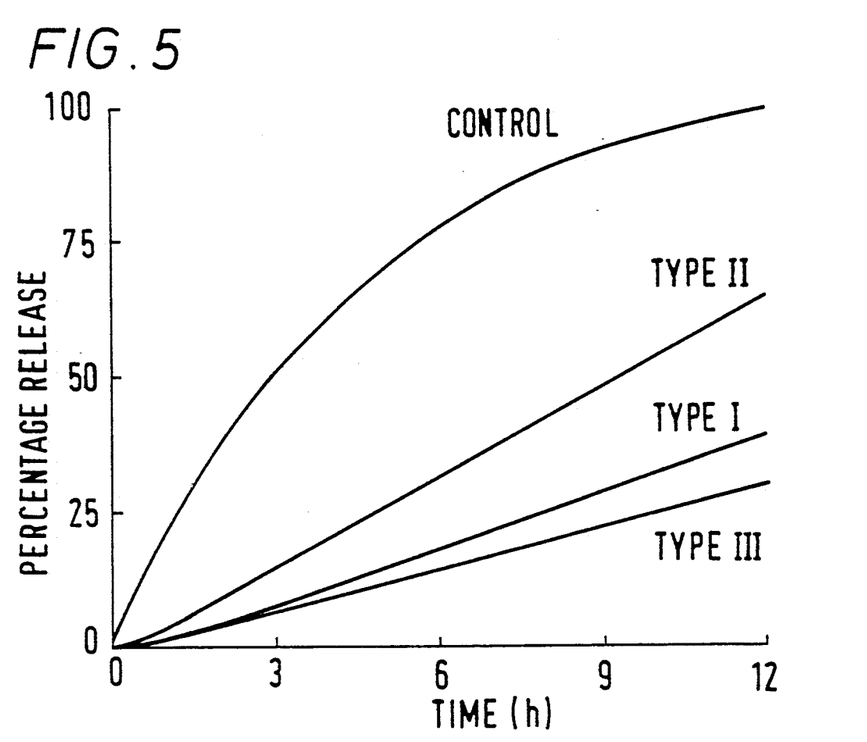
FIG. 5 shows drug release profiles of sprayed liposome suspensions prepared from the three type aerosols.
Figure 6:
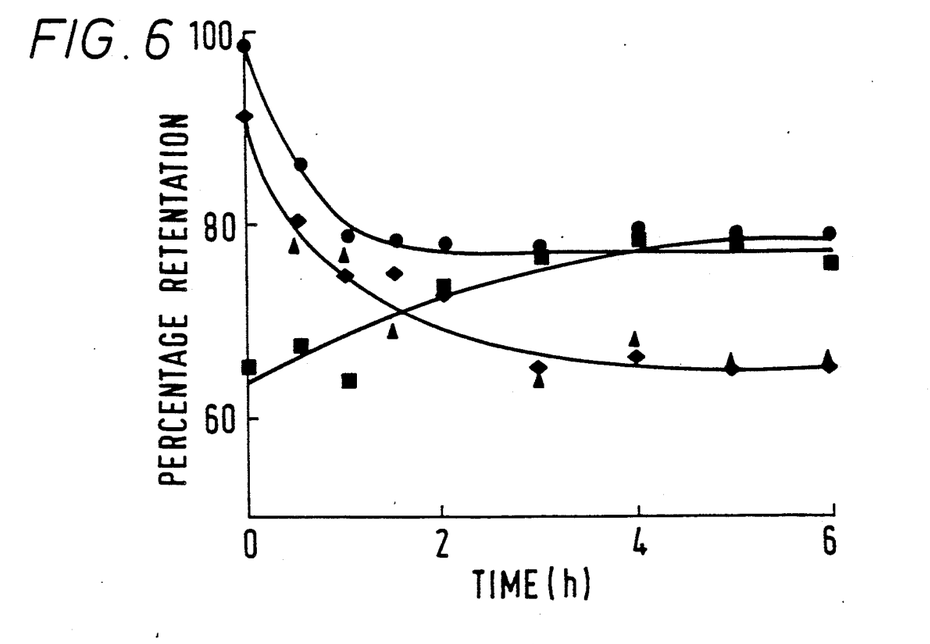
FIG. 6 shows fenoterol retention profiles of liposome suspensions prepared from a powder comprising fenoterol suspended in a lipid.

It can be seen from FIG. 5 that all three pro-liposome aerosol compositions markedly delayed the release of fenoterol (compared to a control solution of the drug) over a period of 12 hours. FIG. 5 shows sustained release profiles of sprayed liposome suspensions prepared from Type I, Type II and Type III aerosols. The aerosol pre 
The prolonged effect of the Type I compositions was particularly evident when the interval between initial treatment and subsequent challenge with histamine was increased to 180 minutes. It would appear that after 180 minutes fenoterol protected in the pro-liposome droplet of the invention was twice as active as the unprotected drug. This is shown in Table V.

TABLE V

RANKING ORDER OF THE INVENTION WITH 12:1; 6:1; LIPID/DRUG RATIOS AFTER 180 MINUTES

| Formulation | Type | Fenoterol | Lipid/Drug | n | Sum of Scores |
|---|---|---|---|---|---|
| LH18 | I | 400 μg | 6:1 | 6 | 208.5 |
| LH19 | I | 400 μg | 12:1 | 6 | 190.5 |
| UNPROTECTED DRUG | | | | 6 | 106.00 |
| CONTROL | | | | 6 | 43.00 |

It also appears that with this invention a lipid/drug ratio of 6:1 is as effective as 12:1 in providing sustained bronchodilatory effect after 180 minutes in experimental animals.

The following examples demonstrate the high initial entrapment and improved retention of powder compositions according to the present invention.

EXAMPLE IX 50 mg of micronised fenoterol HBr was dispersed uniformly in a solution of soy-bean lecithin (600 mg) 95% pure in 2 g of Arcton 11. The Arcton 11 was allowed to flash off, leaving behind a dispersion of fenoterol particles in lipid. To this dispersion, 5 g of micronised lactose was added. The resultant powder composition was tumbled in a ball-mill to ensure uniform mixing.

EXAMPLE X

In a variation of this method, the lactose was added to the suspension of fenoterol in Arcton 11 with the lipid in solution. The Arcton 11 was flashed off, leaving behind a uniform powder composition.

In both examples IX and X, the fenoterol was in solid dispersion in the lipid.

EXAMPLE XI (Comparative)

In this example, 50 mg fenoterol was first dissolved in 2 g of ethanol. 600 mg of lipid was solvated in 4 g of Arcton 11. The 2 solutions were combined and loaded gradually onto 5 g of lactose. The solvents were evaporated off in a stream of nitrogen to leave behind a powder composition wherein the drug was *in solution* in the lipid. This example produced a powder composition that resembled the one described by Payne insofar as that the drug was in solution in the lipid.

EXAMPLE XII

The three components were separately added to a ball-mill or air jet microniser to obtain the required particle size and dispersion of drug in lipid. In this case, no solvents were required.

The measurements for initial entrapment and in-vitro release of fenoterol from the four examples IX–XII were carried out in similar fashion to the aerosol compositions. FIG. 6 shows the release of fenoterol as a function of time for the four formulations:

○ Drug in suspension, and lipid dissolved, in Arcton 11. Lactose added, solvents removed by rotary evaporation.

□ Drug and lipid in solution in 2:1 Arcton 11/ethanol (V:V) mixture. Lactose added, solvents removed by rotary evaporation.

◇ Drug in suspension in Arcton 11 containing lipid. Arcton 11 evaporated prior to lactose addition.

Δ Lactose, lipid, drug milled in tumble mill with no solvent addition.

It can be seen that Examples IX, X and XII which have the drug in suspension in the lipid show much higher initial entrapment than the formulation of Example XI. They also retained the drug much better than the formulation of Example XI, where the drug was in solution in the lipid. The reverse curvature of Example XI is believed to indicate a different mechanism of release of the fenoterol which becomes rapidly released into the aqueous phase as the lactose dissolves and then returns by partition into the lipid phase.

Drug entrapment and release profiles of the powder compositions according to the invention may be affected by lipid/drug ratios in like manner to the aerosol compositions previously described. Alternative lipid materials such as hydrogenated lipids may be used in place of soy-bean lecithin without interfering with the sustained release properties of the resulting composition. The compositions of Examples IX and X may be micronised further to obtain an average particle size, ideally between 0.5 and 8 microns, for inhalation applications. Similar release profiles were found for these further micronised compositions.

In all instances the average particle size of the final powder composition should be less than 100 u and preferably below 60 u.

EXAMPLE XIII

A spray formulation was sprayed through a nozzle to give a hydrogenated lipid of high melting point without hydrophilic carrier by forming micronised droplets of the drug in suspension in the lipid from which carrier has volatilised. The resulting material was collected.

Of course lipsomes may also be formed by adding an excess of water to the pro-liposome powder composition comprising carrier, lipid and drug, the composition being free from other solvent for the lipid. In that case, the powder is simply contacted with excess water without first being dispersed in air. The invention therefore provides a pro-liposome composition wherein a membrane lipid and a particulate biologically active compound are minor components of discrete micronised particles whose major component is a physiologically acceptable solid carrier. The invention also includes making liposomes from a composition as aforesaid by contact with water either in situ or in-vivo. For oral administration the discrete micronised solid particles may be filled into gelatin or other capsules.

The invention further comprises the administration to a human or animal subject of an aerosol composition as aforesaid for the treatment of bronchial, pulmonary and nasal disorders such as asthma, bronchitis, hay fever and the like containing bronchodilators and steroids, antibiotics, anti-histamines or vasoconstrictors. The invention yet further includes the administration of topical preparations where sustained release of the active compound or compounds is desirable, for example in the treatment of psoriasis and inflammatory skin conditions such as eczema with steroids.

I claim:

1. A method for the preparation of a pro-liposome composition, which method comprises:
providing a membrane lipid that on contact with water forms vesicles comprising lipid bilayers surrounding an aqueous space; and
uniformly dispersing discrete micronised particles of a biologically active compound in the membrane lipid, said dispersing being performed in the presence of a solvent for the lipid bi-layer, said solvent not being a solvent for the biologically active compound.

2. A method according to claim 1, wherein the membrane lipid is selected from the group consisting of natural or hydrogenated lecithin, a glycolipid, a long chain dialkyl ammonium compound and a mixture of any of the aforesaid compounds with a compatible lipophilic material.

3. A method according to claim 1, wherein the biologically active compound is selected from the group consisting of bronchodilators, steroids, antibiotics, antihistamines, vasoconstrictors and anti-inflammatory compounds.

4. A method according to claim 1, wherein the biologically active compound is selected from the group consisting of salbutamol, terbutaline, orciprenaline, isoprenaline, reproterol, pirbuterol, butenoside, beclamethasone dipropionate, sodium chromoglycate, fenoterol, ipratropium, betamethasone valerate, rimiterol and ketotifen.

5. A method according to claim 1, wherein the biologically active compound is dispersed in the lipid in the form of particles of average size from 0.5 to 8 micrometers.

6. A method of making vesicles which comprises contacting the pro-liposome composition of claim 1 with water.

7. A method according to claim 6, wherein the contact is in vivo.

8. A method according to claim 6, wherein the contact is in vitro.

9. A method for the preparation of a pro-liposome composition in the form of a powder, which method comprises:
providing a membrane lipid that on contact with water forms vesicles comprising lipid bilayers surrounding an aqueous space, and providing a biologically active compound; and
dispersing the biologically active compound in the membrane lipid while forming discrete micronised solid particles of the biologically active compound suspended in the lipid.

10. A method according to claim 9, wherein while forming the discrete micronized solid particles, there is further provided a carrier in an amount such that in the micronised solid particles formed the lipid and the biologically active compound together are a minor component of said particles and the solid carrier is the major component of said particles.

11. A method according to claim 10, wherein the carrier is selected from glucose and lactose.

12. A method according to claim 10, wherein the weight ratio of membrane lipid to carrier is from 1:1 to 1:25.

13. A method according to claim 12, wherein the weight ratio biologically active compound to lipid is from 1:0.5 to 1:25.

14. A method according to claim 12, wherein the weight ratio of biologically active compound to lipid is from 1:6 to 1:20.

15. A method according to claim 9, wherein the biologically active compound is dispersed in the membrane lipid before the micronised particles are formed by adding the biologically active compound in micronised form to a solution of the membrane lipid in a solvent therefor and allowing the solvent to evaporate.

16. A method according to claim 9, wherein the biologically active compound is dispersed in the membrane lipid by milling simultaneously with formation of the micronised solid particles.

17. A method according to claim 9, wherein the membrane lipid is selected from the group consisting of natural or hydrogenated lecithin, a glycolipid, a long chain dialkyl ammonium compound and a mixture of any of the aforesaid compounds with a compatible lipophilic material.

18. A method according to claim 9, wherein the biologically active compound is selected from the group consisting of bronchodilators, steroids, antibiotics, antihistamines, vasoconstrictors and anti-inflammatory compounds.

19. A method according to claim 9, wherein the biologically active compound is selected from the group consisting of salbutamol, terbutaline, orciprenaline, isoprenaline, reproterol, pirbuterol, butenoside, beclamethasone dipropionate, sodium chromoglycate, fenoterol, ipratropium, betamethasone valerate, rimiterol and ketotifen.

20. A method of making vesicles which comprises contacting the pro-liposome composition of claim 9 with water.

21. A method according to claim 20, wherein the contact is in vivo.

22. A method according to claim 20, wherein the contact is in vitro.

23. A method for forming an aerosol of particles that have the property of spontaneously forming vesicles on contact with an excess of water, said method comprising the step of introducing into a moving air stream solid particles which are the result of micronising together a lipid, a biologically active compound insoluble in said lipid, and a physiologically acceptable carrier in the absence of liquid so that the biologically active compound is present in the aerosol as discrete micronised particles.

24. A method according to claim 23, wherein the lipid is selected from the group consisting of a natural or hydrogenated lecithin, a glycolipid, a long chain dialkyl ammonium compound, and a mixture of the aforesaid compounds with a compatible lipophilic material.

25. A method according to claim 23, wherein the biologically active compound is selected from the group consisting of bronchodilators, steroids, antibiotics, antihistamines, vasoconstrictors and anti-inflammatory compounds.

26. A method according to claim 23, wherein the biologically active compound is selected from the group consisting of salbutamol, terbutaline, orciprenaline, isopronaline, reproterol, pirbuterol, butenoside, beclamethasone dipropionate, sodium chromoglycate, fenoterol, ipratropium, betamethasone valerate, rimiterol and ketotifen.

27. A method according to claim 23, wherein the biologically active compound is dispersed in the lipid in the form of particles of average size from 0.5 to 8 micrometers.

28. A method according to claim 23, wherein the carrier is a member selected from the group consisting of glucose, lactose, a dextran and a starch.

29. A method according to claim 23, wherein the weight ratio of membrane lipid to carrier is from 1:1 to 1:25.

30. A method according to claim 23, wherein the weight ratio of biologically active compound to lipid is from 1:0.5 to 1:25.

31. A method according to claim 30, wherein the weight ratio of biologically active compound to lipid is from 1:6 to 1:20.

* * * * *